United States Patent [19]

Brzosko et al.

[11] Patent Number: 4,558,011

[45] Date of Patent: Dec. 10, 1985

[54] METHOD FOR PREPARATION OF PURE HEPATITIS B SURFACE ANTIGEN FROM HUMAN PLASMA

[75] Inventors: Witold Brzosko; Piotr Janicki; Zbigniew Laskowski; Kazimierz Madalinski; Andrzej Dabrowa, all of Warsaw, Poland

[73] Assignee: Akademia Medyczna, Warsaw, Poland

[21] Appl. No.: 386,182

[22] Filed: Jun. 7, 1982

[30] Foreign Application Priority Data

Jun. 10, 1981 [PL] Poland ................................. 231588

[51] Int. Cl.⁴ .......................... C07G 7/00; A61K 39/29
[52] U.S. Cl. ...................................... 435/272; 424/88; 424/89; 260/112 R; 435/68
[58] Field of Search ............... 424/89, 88; 435/68, 435/235, 267–272; 260/112 R

[56] References Cited

U.S. PATENT DOCUMENTS

| | | | |
|---|---|---|---|
| 3,636,191 | 1/1972 | Blumberg et al. | 424/89 |
| 3,886,270 | 5/1975 | Ackermann | 435/239 |
| 4,017,360 | 4/1977 | Bertland et al. | 424/89 |
| 4,118,479 | 10/1978 | Prince et al. | 424/89 |
| 4,138,287 | 2/1979 | Andersson et al. | 435/239 |

FOREIGN PATENT DOCUMENTS 810811  3/1981  U.S.S.R. ............................ 435/235

*Primary Examiner*—Blondel Hazel
*Attorney, Agent, or Firm*—Mason, Fenwick & Lawrence

[57] ABSTRACT

Method for preparation of pure hepatitis B surface antigen HBsAg from human plasma, wherein the initial plasma after being treated to remove lipides and partially remove human plasma proteins, is submitted to digestion with pepsin in amount of 0.01–0.50 mg/mg of protein to selectively decompose the plasma proteins while the antigen remains intact, filtered in a phosphate buffered medium, up to a pH value of 7.1–7.3, through molecular filters passing molecules of up to 100,000 Daltons, the infectiosity being subsequently deactivated by means of formaldehyde, in proportion of 1:2000 by volume, for 96 hours.

3 Claims, No Drawings

METHOD FOR PREPARATION OF PURE HEPATITIS B SURFACE ANTIGEN FROM HUMAN PLASMA

This invention relates to a method for preparation of pure hepatitis B surface antigen /HBsAg/ from human plasma. The HBsAg is a viral protein occurring in the blood of people suffering from the infectious hepatitis, Type B, or being permanently present in the blood of carriers of hepatitis B virus. HBsAg on being purified from the remaining plasma proteins constitutes a vaccine for infectious hepatitis B, which on being administered to a human or an animal causes the production of HBs antibodies within the patient's organism. Such antibodies protect the host from full infection that is from one caused by the infectiously active particle of hepatitis B virus.

There is known a method for preparation of pure HBsAg through multiple centrifuging of suitably prepared plasma in density gradients obtained from saccharose or caesium chloride. In the method for separation in density gradient through ultracentrifugation; that is through centrifugation with high speeds, preparations of HBsAg can be obtained liberated of resting plasma proteins. The ultracentrifugation method is a very time-consuming one, it requires numerous expensive apparatus to be employed, being, thus, utilized for obtaining small amounts of the antigen for research purposes only. Thus, this approach is suitable for a laboratory method but not for a production procedure. In this method it is not possible to obtain quantities of material necessary for immunizing through vaccination even a relatively moderately sized group of persons.

Further, there are known other methods for preparation of HBsAg, consisting of filtration through gel packed columns, on affinity chromatography, and on electrophoresis. All such methods do fail to obtain antigen preparations completely purified, are essentially laboratory in character, and have a small production output.

According to the invention, the method for preparation of pure HBsAg consists therein that the initial material being deprived from lipides and partially from human plasma proteins, is submitted to digesting with pepsin in amount of 0.01–0.50 mg/mg of protein, preferably of 0.05 mg/mg of protein, filtered off on molecular filters allowing to pass molecules of up to 100,000 Daltons in a phosphate buffered medium, up to the pH value of 7.1–7.3, the infectiosity being subsequently desactivated by means of formaldehyde, preferably in a proportion of 1:2000 by volume, for 96 hours. The method according to the invention, in contradistinction to known methods, gives the HBsAG completely liberated from plasma proteins. The resultant antigen when employed as a vaccine for infectious hepatitis, Type B, does not cause any side effects to the patient being vaccinated. Moreover, the method according to the invention can be utilized in large scale production of vaccine from the plasma containing hepatitis B virus protein.

The preparation of the purified hepatitis B surface antigen in the method according to the invention proceeds as follows.

In the first phase the delipidization of human plasma is conducted. Therefor, 1000 ml of plasma obtained from donors of HBsAg, having the titer as determined in the immunoelectroosmoprecipitation /IEOP/ of at least 1:10 obtain an addition of 1000 ml of 0.1 mole of $MnCl_2.4H_2O$.

After addition of manganium chloride the plasma is stirred in an electromagnetic agitator at the temperature of ice bath for 1 hour. Then the material is centrifuged for 30 minutes with a speed of 6000 rpm. After centrifugation the precipitation is rejected, containing no HBsAg.

The supernatant liquid obtained after centrifugation is brought to the pH value of 5.6 using 0.1 HCl and polyethylene glycol 6000 /PEG 6000/ is added in amount of 75 g per 1000 ml of the material. Then the material is subjected to stirring for about 12 hours at the temperature of 4° C. in an electromagnetic agitator. The material after being discharged from the agitator is centrifuged for 30 minutes with a speed of 6000 rpm. The supernatant liquid containing no antigen is rejected, and for further processing the sediment is collected, obtained from the centrifugation.

This sediment is dissolved in 200 ml of 0.9 NaCl, and the solution is made-up with deionized water to the volume shown by the material before being centrifuged. After addition of NaCl sediment appears in the solution anew. This solution is once more submitted to centrifugation for 30 minutes with a speed of 6000 rpm. After centrifugation the supernatant liquid is collected, containing the HBs antigen, the antigen-free sediment -being rejected. Through addition of deionized water the volume of the supernatant liquid is increased to 10,000 ml. A small amount of sediment remaining after dilution is removed by means of centrifuging in course of 30 minutes with the speed of 6000 rpm. At the further stage of the antigen preparation process, the supernatant liquid obtained by this centrifugation is utilized.

The material prepared in course of the delipidization is now submitted to digesting with an enzyme. Therefor, 10,000 ml of the material is heated up to the temperature of about 37° C., its pH value being standardized to 2.5, by means of addition of 1N HCl. To the material prepared in this way pepsin Sigma is added, crystallized repeatedly, in amount of about 0.05 mg per 1 mg of the solution proteins. The content of proteins in the solution is determined by a spectrophotometric method. After a time of about 1 hour the digesting is interrupted with pepsin through standardizing the solution to the pH value of 4.6 by means of 1N NaOH. After completion of the digesting the solution is centrifuged off for 30 minutes with the speed of 6000 rpm. In the sediment remaining after the centrifugation no HBsAg is detected, being transferred in entirety into the supernatant liquid.

The digesting with pepsin causes a degradation of human plasma proteins into polypeptide units having the size not exceeding 30,000 Daltons. The HBsAg protein does not, however, undergo the digestion.

Next comes the phase of purification of the material from plasma proteins digested with pepsin, by means of molecular filtration on filters letting pass particles up to the size of 100,000 Daltons. For this purpose, a closed-circuit filtering system, manufactured by the AMICON Company—United States, can be employed, wherein the material to be filtered is many times filtered through the filtering zone where particles are discharged from the solution by means of the molecular filters, having the size smaller than the filtering limit. According to the invention, there is employed filtration through a filter of the type H 1×100 letting pass the particles of the size of up to 100,000 Daltons. The full filtering cycle comprises a nine-fold pumping of the material in a volume of 80 liters under a pressure of 0.62 atm. Before the material gets introduced into the filtering system, it is diluted to this volume by means of phosphate buffered, deionized, apyrogenic water. Such water can be produced in an apparatus manufactured by the ELGA Company—Great Britain.

In course of filtering, there is achieved a complete separation of plasma proteins previously digested with pepsin. The material obtained from the filtering system, containing purified HBsAg, is placed in portions of 10,000 ml each in the refrigerator for a time of 96 hours, on adding formaldehyde in amount necessary for to obtain its concentration in the solution of about 1:2000 by volume. After removal from the refrigerator, formaldehyde is removed from the material by means of dedialyzation. Then, it is conducted the adsorption of HBsAg on aluminium hydroxide being added in amount of 1 mg per 1 ml of the solution. The final vaccine obtained in this way is filled into ampoules.

The vaccine obtained in the way described above, when analysed for the presence of human plasma proteins, after the method of double diffusing in agar, does not show precipitation lines at 30-fold thickening with plasma of anit-human proteins. Said vaccine also does not contains infectious particles of hepatitis B virus.

EXAMPLE

From a human donor of HBsAg plasma is collected in the way of plasmaphoresis. The activity of HBsAg gets determined by means of immunoelectroosmophoresis having the titre not lower than 1:16. The human plasma is subjected to the delipidization process through adding—to 1 liter of plasma—1 liter of $0.1M$ $MnCl_2.4H_2O$ and 150,000 Int. units of heparin in a volume of 30 ml. The mixture is incubated at room temperature on an electromagnetic agitator for a time of 0.5 h. After the lapse of this time, the entirety of the material is centrifuged on the centrifuge, Type Beckman J-6, with rotor JA-10 at the speed of 6000 rpm. for a time of 30 minutes. The obtained sediment, being free of HBsAg, is rejected, the supernatant being collected in a flask having the capacity of 2 l.

To the material there are added some amounts of 7.5% of PEG solution, having molecular weight of 6000. The pH value is brought to 5.5 by means of 1N HCl. The material is then placed in a refrigerator and incubated over night under continuous stirring.

The next day, the material is centrifuged off on the Beckman J-6 centrifuge, with rotor JA-10 at 6000 rpm. The supernatant, being HBsAg, is rejected, the sediment being dissolved in 200 ml of 10.9% NaCl and made up with deionized water to the volume of 2 l. After 20-30 minutes abundent sediment appears and is removed through centrifugation on the Beckman J-6 centrifuge, with rotor JA-10 at 6000 rpm in course of 30 minutes. The obtained cleared filtrate shows the activity of HBsAg, using immunoelectroosmophoresis with a titre of 1:8. The volume of the material is then increased up to 10 l with deionized water/2 l+8 l of deionized water/. After 30 minutes, settlement of small amounts of sediment is observed, and is rejected through centrifugation on the Beckman J-6 centrifuge with rotor JA-10 at 6000 rpm for a time of 30 minutes. Clarified supernatant is obtained having a titre of about 1:2 in the immunoelectroosmoprecipitation test.

To 10 l of supernatant there are added 90 g of NaCl, to obtain a 0.9% NaCl solution.

The material prepared in this way is incubated at a temperature of 37° C. for a time of 12 hours. After this time, to the liquid having a teperature of 37° C. and pH=2.5 pepsin is added in amount of 0.05 mg/ml, that is 0.5 g of pepsin per 10 l of material. The pepsin digesting of the solution is conducted for 1 h at the temperature of 37° C. After 1 hour the digestion gets stopped through increasing the pH value up to 3.5 by means of 0.1N NaOH.

The remaining sediment is centrifuged on the Beckman J-6 centrifuge with rotor JA-10 at 6000 rpm. for 20 min, and thereafter rejected.

The supernatant is subjected to the molecular filtration in the apparatus DC 30 of the AMICON Company, with use of hollow fiber filters H 10×100.

By the molecular filtration, material is obtained having the volume of 10 l, the titre whereof in the immunoelectroosmoprecipitation of HBsAg amounts to 1:2.

Such material concentrated 100-fold shows no precipitation lines in the immunodiffusion technique on agar, with use of animal plasma:-anti-IgG, anti-IgM, anti-IgA, antihumen protein, and the plasma antihuman protein.

The vaccination of laboratory animals, such as guinea pigs or rabbits, with a 100-fold concentrated material gives no immunological response against the contamination of the preparation with proteins originated from the human plasma. There is obtained only one precipitation line with the HBsAg containing material.

The material obtained by the described method is highly immunogenic, as proved by vaccinations of chimpanzees, and a dosen or so human volunteers.

| Chemical characteristic of the vaccine for the viral hepatitis B | | |
|---|---|---|
| HBsAg | −0.5 | $\mu g/cm^3$ |
| Total protein | −0.5 | $\mu g/cm^3$ |
| Polypeptides molecular weight of 30,000 | −0.02 | $\mu g/cm^3$ |
| NaCl | −0.85% | |
| Aluminium hydroxide | −1 | $mg/cm^3$ |
| Merthiolate | −100 | $\mu gm/cm^3$ |

In the material the presence of HBcAg, HBeAg, and DNA polymerase has not been formed, when using third generation tests.

What is claimed is:

1. A method for preparing pure hepatitis B surface antigen from human plasma containing hepatitis B antigen which comprises the steps of (a) subjecting said plasma to a delipidization treatment, (b) digesting the thus-treated plasma with pepsin in an amount within the range of 0.05–0.50 mg per mg of plasma protein and for a time sufficient to selectively degrade the plasma proteins in said plasma to a molecular size less than about 100,000 Daltons without degradation of said surface antigen, (c) then filtering the thus-digested plasma through a molecular filter capable of passing therethrough particles up to 100,000 Daltons in size while retaining particles in excess of that size, said digested plasma being diluted prior to such filtration with a phosphate buffered medium having a pH of 7.1–7.3, (d) recovering from said molecular filter the particles in excess of 100,000 Daltons containing said surface antigen and (e) treating the thus-recovered material with formaldehyde at a concentration and for a time sufficient to inactivate any infectious hepatitis B viruses present therein without inactivating said hepatitis B surface antigen.

2. A method as defined in claim 1, characterized in that said recovered material is inactivated with formaldehyde in a concentration of 1:2000 vol./vol. for a time of 96 hours.

3. The method of claim 1 wherein said molecular filter is in the form of hollow fibers.

* * * * *